United States Patent [19]
Galbo et al.

[11] Patent Number: 5,300,544
[45] Date of Patent: Apr. 5, 1994

[54] NON-MIGRATING 1-HYDROCARBYLOXY-2,2,6,6-TETRAMETHYLPIPERDINE 1,3,5-TRIAZINE DERIVATIVES AS POLYMER STABILIZERS

[75] Inventors: James P. Galbo, Wingdale; Ramanathan Ravichandran, Nanuet; Mark S. Holt, West Nyack, all of N.Y.

[73] Assignee: Ciba-Geigy Corporation, Ardsley, N.Y.

[21] Appl. No.: 30,999

[22] Filed: Mar. 12, 1993

Related U.S. Application Data

[62] Division of Ser. No. 878,678, May 5, 1992, Pat. No. 5,216,156.

[51] Int. Cl.$^5$ .......................................... C08K 5/3492
[52] U.S. Cl. ....................................................... 524/00
[58] Field of Search ........................................ 524/100

[56] References Cited

U.S. PATENT DOCUMENTS

| | | | |
|---|---|---|---|
| 4,145,512 | 3/1979 | Uhrhan et al. | 528/73 |
| 4,234,728 | 11/1980 | Rody et al. | 544/198 |
| 4,344,876 | 8/1982 | Berner | 524/91 |
| 4,426,471 | 1/1984 | Berner | 524/91 |
| 4,426,472 | 1/1984 | Berner | 524/99 |
| 4,619,956 | 10/1986 | Susi | 524/87 |
| 4,730,017 | 3/1988 | Avar | 524/103 |
| 4,740,544 | 4/1988 | Nakahara et al. | 524/100 |
| 4,910,238 | 3/1990 | Nakahara et al. | 524/100 |
| 5,019,613 | 5/1991 | Ravichandran et al. | 524/100 |
| 5,096,950 | 3/1992 | Galbo et al. | 524/102 |
| 5,112,890 | 5/1992 | Behrens et al. | 524/102 |
| 5,145,893 | 9/1992 | Galbo et al. | 524/102 |
| 5,169,925 | 12/1992 | Schmailzl et al. | 524/95 |
| 5,171,855 | 12/1992 | Borzatta et al. | 524/95 |
| 5,214,084 | 5/1993 | Ishii et al. | 524/102 |

OTHER PUBLICATIONS

J. Org. Chem. vol. 96, No. 1 (1971) pp. 209–211.
Millar et al., Radiation Research 88, 369–376 (1981).
Callais et al. High Solids Coating Compositions containing polymer-bound light stabilizer acrylic resins pp. 486–504.

*Primary Examiner*—Kriellion S. Morgan
*Attorney, Agent, or Firm*—Luther A. R. Hall

[57] ABSTRACT

1-Hydrocarbyloxy-2,2,6,6-tetramethylpiperidine derivatives of s-triazines having functional groups such as hydroxy, amino, carboxy, epoxy, isocyanate or the like present are capable of chemically bonding with polymer substrates having anhydride, epoxide, alkoxymethylmelamine or isocyanate moieties present. This chemical bonding prevents migration or loss of the stabilizer during subsequent processing or end-use application of the stabilized polymer.

11 Claims, No Drawings

NON-MIGRATING 1-HYDROCARBYLOXY-2,2,6,6-TETRAMETHYL-PIPERDINE 1,3,5-TRIAZINE DERIVATIVES AS POLYMER STABILIZERS

This is a divisional of application Ser. No. 07/878,678, filed on May 5, 1992, now U.S. Pat. No. 5,216,156, granted on Jun. 1, 1993.

The instant invention pertains to novel, non-migrating 1-hydrocarbyloxy-2,2,6,6-tetramethylpiperidine s-triazine derivatives and compositions stabilized therewith.

BACKGROUND OF THE INVENTION

Specific 1-hydrocarbyloxy 2,2,6,6-tetramethylpiperidine derivatives bearing a reactive functional group have been described in end-use applications other than polymer stabilization. For example, 1-benzyloxy-4-hydroxy-2,2,6,6-tetramethylpiperidine has been detected during the photolysis of 4-hydroxy-1-oxyl-2,2,6,6-tetramethylpiperidine in toluene (J. F. W. Keana, *J. Org. Chem.*, 36, 209 (1971). A salt of 1-[1-(2-cyano-2-propyl)oxy-2,2,6,6-tetramethylpiperidin-4-yl]-amino-3-(2-nitro-1-imidazolyl)-2-prop anol has been used in a study of nitroxyl radiosensitizers (B. C. Millar et al., *Radiat. Res.*, 88, 369 (1988).

U.S. Pat. Nos. 4,619,956; 4,426,471; 4,426,472; 4,344,876 and 4,234,728 include hindered amine substituted N-(hydroxyalkyl)amino and N-(alkoxymethyl)amino substituted s-triazine derivatives. However, none of these patents teaches the use of 1-hydrocarbyloxy substituted hindered amines as polymer stabilizers.

U.S. Pat. No. 4,740,544 claims, but does not exemplify bisphenol A bridged N-(hydroxyalkyl)amino-N-(1-alkoxy-2,2,6,6-tetramethylpiperidin-4-yl)-1,3,5-triazine compounds as polymer stabilizers. This patent does not teach any advantages of using 1-hydrocarbyloxy substituted hindered amine polymer stabilizers.

The use of reactable stabilizers in certain polymer substrates has been described. For example, U.S. Pat. Nos. 4,145,512 and 4,178,279 describe the stabilization of urethanes by molecules which contain combinations of hindered amines and amino, hydroxy or hydrazide groups. The stabilizer molecules are introduced into the prepolymer solution. Aminooxamide hindered amine derivatives have been reacted with acrylic polyols containing anhydride groups (P. A. Callais et al., *Proc. Water-Borne High-Solids Coat. Symp.*, 16, 486 (1989). The use of hydroxy substituted 4-oxamido hindered amine derivatives is taught in U.S. Pat. No. 4,730,017. The use of 1-hydrocarbyloxy substituted hindered amines as polymer stabilizers is not disclosed in these patent.

U.S. Pat. No. 4,910,238 discloses several s-triazine derivatives containing a bis(2-hydroxyethyl)amino or a 2-hydroxyethylamino substituent. There is no overlap between the instant compounds and those of this patent.

The advantages of the reduced basicity of 1-hydrocarbyloxy substituted hindered amines as polymer stabilizers in acid sensitive polymer substrates is first described in copending U.S. patent application Ser. No. 749,470 abandoned. N-Hydrocarbyloxy derivatives of hindered amine substituted s-triazines are disclosed in copending U.S. patent applications Ser. Nos. 749,470 and 727,340 abandoned; and U.S. Pat. No. 5,019,613 U.S. Pat. No. 5,118,736. None of these applications and patent includes compounds with reactive functional groups.

Copending U.S. patent application Ser. No. 480,173 U.S. Pat. No. 5,145,893 describes the use of non-migrating 1-hydrocarbyloxy hindered amine derivatives as polymer stabilizers. However, the compounds disclosed in application Ser. No. 480,173 U.S. Pat. No. 5,145,893 differ substantially from the s-triazine derivatives described in the instant invention.

OBJECTS OF THE INVENTION

One object of the instant invention is to provide novel 1-hydrocarbyoxy-2,2,6,6-tetramethylpiperidine derivatives of s-triazines which can be incorporated into polymer substrates by a chemical condensation reaction.

Another object of the invention is to provide stabilized compositions having an effective stabilizing amount of said s-triazine derivatives chemically bonded onto the substrate being stabilized.

DETAILED DISCLOSURE

The instant invention pertains to stabilized compositions of matter containing novel 1-hydrocarbyloxy 2,2,6,6-tetramethylpiperidine s-triazine derivatives which are incorporated into a polymer substrate by a condensation reaction. The instant compounds have hydroxy, amino, carboxy, epoxy, isocyanate, silyloxy, or (alkoxymethyl)amino functional groups which are capable of reacting with anhydride, epoxide, alkoxymethylmelamine, isocyanate, or hydroxy groups present in the polymer substrate. The stabilizer molecule is therefore bound to the polymer substrate during processing and end-use. The instant stabilizer molecules are distinguished from other types of stabilizer molecules which contain vinyl groups and would be chemically bound to a polymer substrate by a free radical polymerization reaction.

The instant stabilizer molecules are especially effective in acid catalyzed and ambient cured coatings systems. Examples of such systems include thermoset acrylic resins with melamine crosslinking agents, acrylic alkyd or polyester resins with isocyanate crosslinking agents, and epoxide resins with carboxylic acid, anhydride, or amine crosslinking agents.

The instant invention pertains to a 1-hydrocarbyloxy 2,2,6,6-tetramethylpiperidine s-triazine compound of formula I, II, III, IV, V, VI, VII, VIII, IX, X or XI

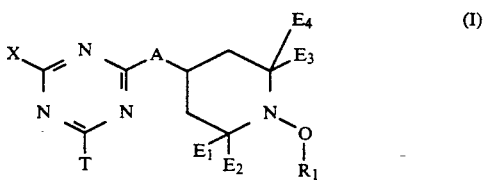

(I)

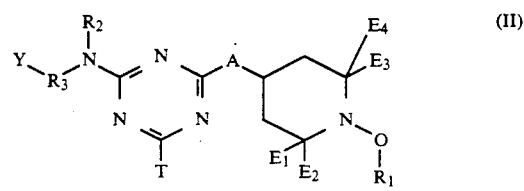

(II)

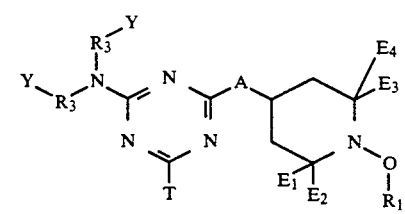 (III)

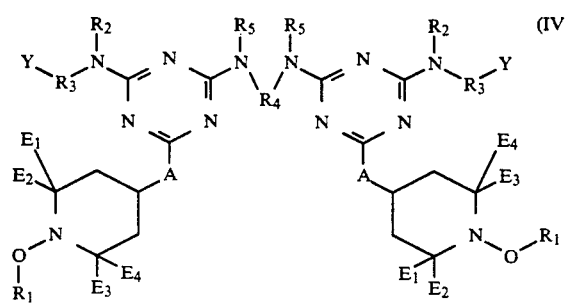 (IV)

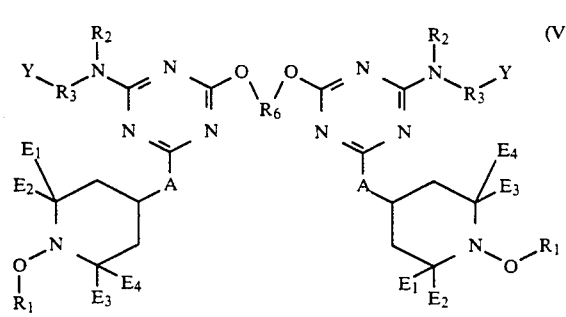 (V)

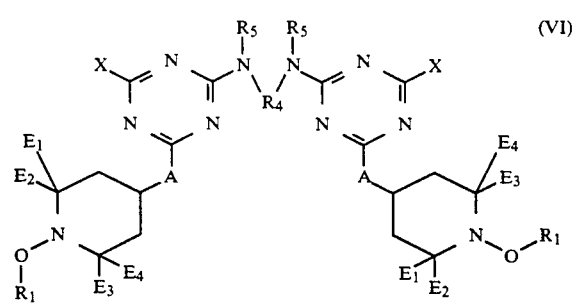 (VI)

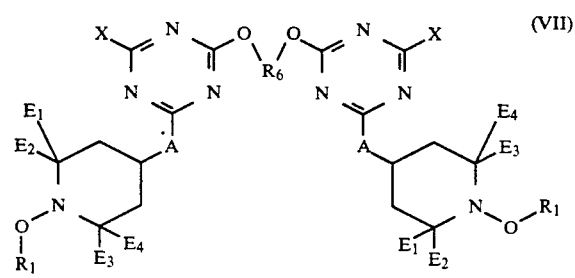 (VII)

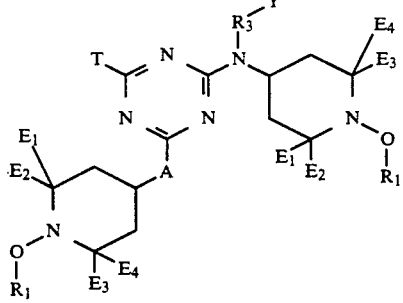 (VIII)

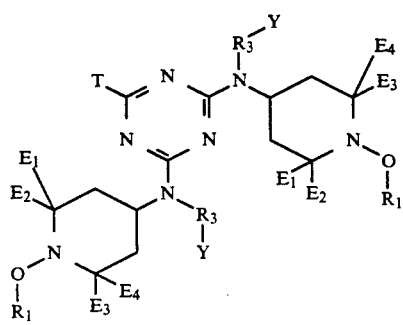 (IX)

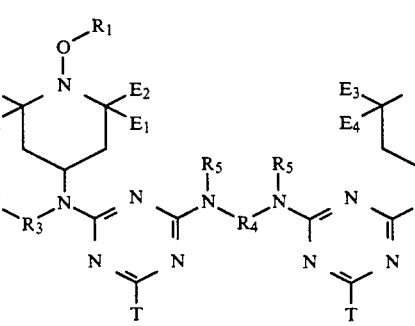 (X)

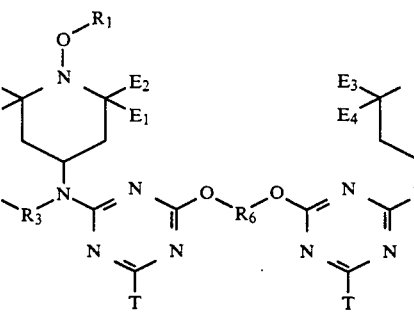 (XI)

wherein $E_1$, $E_2$, $E_3$ and $E_4$ are independently alkyl of 1 to 4 carbon atoms, or $E_1$ and $E_2$ are independently alkyl of 1 to 4 carbon atoms and $E_3$ and $E_4$ taken together are pentamethylene, or $E_1$ and $E_2$; and $E_3$ and $E_4$ each taken together are pentamethylene, $R_1$ is alkyl of 1 to 18 carbon atoms, cycloalkyl of 5 to 12 carbon atoms, a bicyclic or tricyclic hydrocarbon radical of 7 to 12 carbon atoms, phenylalkyl of 7 to 15 carbon atoms, aryl of 6 to 10 carbon atoms or said aryl substituted by one to three alkyl of 1 to 8 carbon atoms, $R_2$ is hydrogen or a linear or branched chain alkyl of 1 to 12 carbon atoms, $R_3$ is alkylene of 1 to 8 carbon atoms, or $R_3$ is —CO—, —CO—$R_4$—, —CONR$_2$—, or —CO—NR$_2$—R$_4$—, $R_4$ is alkylene of 1 to 8 carbon atoms,
$R_5$ is hydrogen, a linear or branched chain alkyl of 1 to 12 carbon atoms, or

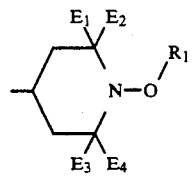

or when $R_4$ is ethylene, two $R_5$ methyl substituents can be linked by a direct bond so that the triazine bridging group —N($R_5$)—$R_4$—N($R_5$)— is a piperazin-1,4-diyl moiety, $R_6$ is alkylene of 2 to 8 carbon atoms or $R_6$ is

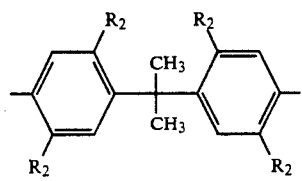

with the proviso that Y is not —OH when $R_6$ is the structure depicted above,

A is —O— or —N$R_7$— where $R_7$ is hydrogen, a straight or branched chain alkyl of 1 to 12 carbon atoms, or $R_7$ is

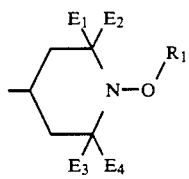

T is phenoxy, phenoxy substituted by one or two alkyl groups of 1 to 4 carbon atoms, alkoxy of 1 to 8 carbon atoms or —N($R_2$)$_2$ with the stipulation that $R_2$ is not hydrogen, or T is

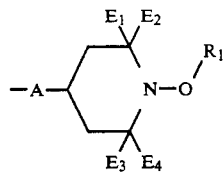

X is —NH$_2$, —NCO, —OH, —O—glycidyl, or —NHNH$_2$, and

Y is —OH, —NH$_2$, —NH$R_2$ where $R_2$ is not hydrogen; or Y is —NCO, —COOH, oxiranyl, —O—glycidyl, or —Si(O$R_2$)$_3$; or the combination $R_3$—Y— is —CH$_2$CH(OH)$R_2$ where $R_2$ is alkyl or said alkyl interrupted by one to four oxygen atoms, or $R_3$—Y— is —CH$_2$O$R_2$.

Preferably $E_1$ to $E_4$ are each methyl.
Preferably $R_1$ is cyclohexyl, octyl, methyl, or heptyl;
$R_2$ is hydrogen, butyl, or dodecyl;
$R_3$ is ethylene when Y is —OH or $R_3$ is pentamethylene when Y is —COOH;
$R_4$ is ethylene or hexamethylene;
$R_5$ is hydrogen or

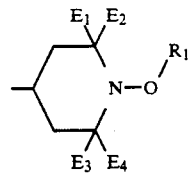

$R_6$ is

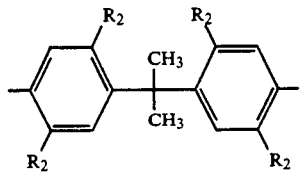

A is —N($R_7$)— wherein $R_7$ is butyl;
T is

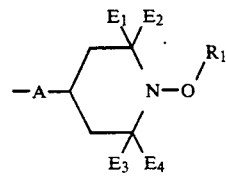

X is —NH$_2$, —O—glycidyl, or —NCO;
Y is —OH or —COOH; and $R_3$—Y is —CH$_2$OCH$_3$.

The instant invention also pertains to compositions stabilized against the deleterious effects of heat, oxygen and actinic light which comprise (a) synthetic polymer, and (b) an effective stabilizing amount of a compound of formula I, II, III, IV, V, VI, VII, VIII, IX, X or XI, as described above.

More particularly, the synthetic polymer of component (a) is an acid catalyzed or ambient temperature cured polymer selected from the group consisting of thermoset acrylic resins with melamine crosslinking agents, acrylic alkyd or polyester resin with isocyanate crosslinking agents or epoxy resins with carboxylic acid, anhydride or amine crosslinking agents.

More particularly, the compound of component (b) is bonded onto the polymer substrate of component (a) through a chemical bond derived from the chemical reaction of the functional group present in the compound of component (b) with an appropriately reactive functional group on the substrate polymer of component (a).

There are clear advantages in using the hindered amine compounds having 1-hydrocarbyloxy substitution. In certain polymer systems, there is a definite advantage in using a less basic stabilizer. For example, the cure of acid-catalyzed thermoset melamine crosslinked automotive coatings systems can be severely retarded by an interaction between the acid catalyst and a basic hindered amine stabilizer. N-Hydrocarbyloxy hindered amines are significantly less basic than the corresponding N-H or N-alkyl hindered amines. The reduced basicity of N-hydrocarbyloxy hindered amines is shown in Table 1.

TABLE 1

| Hindered Amine Basicity | |
|---|---|
| Substituent* | $pK_a$ |
| N—H | 10.0 |
| N—Me | 10.0 |
| N—OMe | 4.8 |

*derivatives of 4-hydroxy-2,2,6,6-tetramethylpiperidine

When any of the aforementioned groups $R_1$ to $R_6$ and T are alkyl, they are, for example, methyl, ethyl, isopropyl, n-butyl, sec-butyl, tert-butyl, isoamyl, n-hexyl, heptyl, 2-ethylhexyl, isooctyl, tert-octyl, nonyl, decyl, undecyl, lauryl, tridecyl, tetradecyl, hexadecyl, heptadecyl and octadecyl and branched isomers thereof; when cycloalkyl, they are, for example, cyclopentyl, cyclohexyl, cyclooctyl and cyclododecyl; when aralkyl, they are, for example, benzyl, phenethyl, α-methylbenzyl and α,α-dimethylbenzyl; when aryl, they are, for example, phenyl, 1-naphthyl and 2-naphthyl; when substituted phenyl, they are, for example, tolyl, xylyl, ethylphenyl, tert-butylphenyl and tert-dodecylphenyl; and when alkylene, they are, for example, methylene, ethylene, tetramethylene, hexamethylene and octamethylene.

The instant compounds are prepared by the reaction of 1-hydrocarbyloxy derivatives of 4-amino, 4-alkylamino-, or 4-hydroxy-2,2,6,6-tetramethylpiperidine with cyanuric chloride or an appropriately substituted derivative of cyanuric chloride as described in copending application Ser. No. 749,470 and U.S. Pat. No. 5,019,613. The reactable functional groups are attached using standard synthetic methodology.

The synthesis of 1-hydrocarbyloxy hindered amine derivatives have been described. For example, N-methoxy derivatives of 2,2,6,6-tetramethylpiperidine are synthesized as disclosed in copending application Ser. No. 749,470 by reaction of an appropriate N-oxyl precursor with methyl radicals generated by the thermolysis of di-tert-butyl peroxide in an inert solvent such as chlorobenzene. N-Hydroxy piperidines, prepared by the oxidation of a hindered amine with an organic hydroperoxide and metal oxide catalyst followed by catalytic hydrogenation, as described in U.S. Pat. No. 4,831,134, can be alkylated by reaction with sodium hydride and an alkyl halide (T. Kurumada et al., J. Poly. Sci., Polym. Chem. Ed., 23, 1477 (1985). The preferred method of synthesis of 1-hydrocarbyloxy derivatives of hindered amines involves the thermal reaction of a hydrocarbon solution of a hindered amine or its N-oxyl derivative with tert-butyl hydroperoxide and a metal oxide catalyst as taught in U.S. Pat. No. 4,921,962. Synthesis of the 1-hydrocarbyloxy derivatives of 4-amino-, 4-alkylamino-, and 4-hydroxy-substituted hindered amines required for the preparation of the instant triazine derivatives is taught in copending patent applications Ser. Nos. 749,470 and 480,173; and U.S. Pat. No. 5,021,481.

The preferred method for preparing many of the instant compounds is to react two equivalents of 4-hydroxy-2,2,6,6-tetramethylpiperidine or a 4-alkylamino-2,2,6,6-tetramethylpiperidine with cyanuric chloride followed by introduction of the 1-hydrocarbyloxy moiety using tert-butyl hydroperoxide, a hydrocarbon solvent, and a metal oxide catalyst as taught in U.S. Pat. No. 4,921,962. The resulting chloro-s-triazine intermediate is subsequently reacted with the appropriate reagent in order to introduce the reactable functionality.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate: mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from α,β-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S. Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.

32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants 1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol 1.2. Alkylated hydroquinones, for example,
2,6-di-tert-butyl-4-methoxyphenol
2,5-di-tert-butyl-hydroquinone 2,5-di-tert-amyl-hydroquinone
2,6-diphenyl-4-octadecyloxyphenol 1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example,
1,3,5-tri-(3,5-di-tert-butyl-4-hydroxybenzy)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example,
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers
2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrolotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl) sebacate.

2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2-hydroxyethoxy)phenyl]6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearylsorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerylthritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl N-heptadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinammate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocyanurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of
bis(2,2,6,6-tetramethylpiperidin-4-yl) sebacate,
bis(1,2,2,6,6-pentamethylpiperidin-4-yl) sebacate, di(1,2,2,6,6-pentamethylpiperidin-4-yl) (3,5-di-tert-butyl-4-hydroxybenzyl)butylmalonate,
4-benzoyl-2,2,6,6-tetramethylpiperidine, 4-stearyloxy-2,2,6,6-tetramethylpiperidine,
3-n-octyl-7,7,9,9-tetramethyl-1,3,8-triaza-spiro[4.5]decane-2,4-dione,
tris(2,2,6,6-tetramethylpiperidin-4-yl) nitrilotriacetate,
1,2-bis(2,2,6,6-tetramethyl-3-oxopiperazin-4-yl)ethane,
2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine),
polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane,
tetrakis(2,2,6,6-tetramethylpiperidin-4-yl) 1,2,3,4-butanetetracarboxylate,
tetrakis(1,2,2,6,6-pentamethylpiperidin-4-yl) 1,2,3,4-butanetetracarboxylate,
polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazin-2-yl]-1,10-diamino-4,7-diazadecane,
mixed [2,2,6,6-tetramethylpiperidin-4-yl/$\beta,\beta,\beta',\beta'$-tetramethyl-3,9-(2,4,8,10-tetraoxaspiro[5.5]-undecane) diethyl] 1,2,3,4-butanetetracarboxylate,
mixed [1,2,2,6,6-pentamethylpiperidin-4-yl/$\beta,\beta,\beta',\beta'$-tetramethyl-3,9-(2,4,8,10-tetraoxaspiro[5.5]-undecane)diethyl] 1,2,3,4-butanetetracarboxylate, octamethylene bis(2,2,6,6-tetramethylpiperidin-4-carboxylate),
4,4'-ethylenebis(2,2,6,6-tetramethylpiperazin-3-one), and
bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperidine and succinic acid, the polycondensation product of 2,4-dichloro-6-tert-octylamino-s-triazine and 4,4'-hexamethylenebis-(amino-2,2,6,6-tetramethylpiperidine), N,N',N'',N'''-tetrakis[4,6-bis(butyl-(2,2,6,6-tetramethyl-piperidin-4-yl)amino)-s-triazine-2-yl]-1,10-diamino-4,7-diazadecane or bis(1-octyloxy-2,2,6,6-tetramethylpiperidin-4-yl) sebacate.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent bright-stocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: G$_1$-OCC-alkylene-COOG$_2$ wherein "alkylene" denotes an alkylene residue having from 2 to 14 carbon atoms and G$_1$ and G$_2$ are the same or different and each is an alkyl group having from 6 to 18 carbon atoms. Tri-esters which are of use as lubricating oil base stocks are those derived from trimethylolpropane and C$_6$-C$_{18}$ mono-carboxylic acids or mixtures thereof, whereas suitable tetra-esters include those derived from pentaerythritol and a C$_6$-C$_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of phenolic antioxidants
1. Alkylated Monophenols
2,6-Di-tert-butyl-4-methylphenol, 2,6-di-tert-butylphenol, 2-tert-butyl-4,6-dimethylphenol, 2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-($\beta$-methylcyclohexyl)-4,6-dimethylphenol, 2,6-di-octa-decyl-4-methylphenol, 2,4,6-tricyclohexylphenol, 2,6-di-tert-butyl-4-methoxymethylphenol, o-tert-butylphenol.

2. Alkylated Hydroquinones
2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers
2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols
2,2'-Methylene-bis-(6-tert-butyl-4-methylphenol), 2,2'-methylene-bis-(6-tert-butyl-4-ethylphenol), 2,2'-methylene-bis-(4-methyl-6-($\alpha$-methyl-cyclohexyl)-phenol), 2,2'-methylene-bis-(4-methyl-6-cyclohexyl-phenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-($\alpha$-methylbenzyl-4-nonylphenol), 2,2'-methylene-bis-(6-($\alpha,\alpha$-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methylphenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methyl-phenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, di-hydroxyethyl-oxalic acid diamide. 9. Amides of β-(3,5-Di-tert-butyl-4-hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants:

N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diamino-diphenyl-methane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allylphenothiazine, tert-octylated phenothiazine, 3,7-di-tert-octylphenothiazine.

Examples for other antioxidants:

Aliphatic or aromatic phosphites, esters of thiodipropionic acid or of thiodiacetic acid, or salts of dithiocarbamic or dithiophosphoric acid.

Examples of metal passivators, for example for copper, are:

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

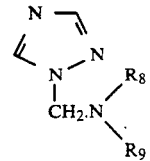

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g.

I. Primary, secondary or tertiary aliphatic or cycloaliphatic amines and amine-salts or organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula $$R_{12}-X_2-CH_2-CH(OH)-CH_2NR_{13}R_{14}$$

in which $X_2$ is $-O-$, $-S-$, $-SO_2-C(O)-O-$ or $-N(R_d)$ in which $R_{12}$ is H or $C_1-C_{12}$alkyl, $R_{13}$ is unsubstituted $C_1$–$C_4$alkyl or $C_2$–$C_5$alkyl substituted by one to three hydroxyl groups, $R_{14}$ is hydrogen, unsubstituted $C_1$–$C_4$alkyl or $C_2$–$C_5$alkyl substituted by one to three hydroxyl groups provided that at least one of $R_{13}$ and $R_{14}$ is hydroxy-substituted, and $R_{12}$ is $C_2$–$C_{20}$alkyl —$CH_2$—$CH(OH)$—$CH_2NR_{13}R_{14}$ or $R_{12}$ is $C_2$–$C_{18}$alkenyl, $C_2$–$C_3$alkynyl or $C_5$–$C_{12}$cycloalkyl provided that, when $X_2$ is —O— or —C(O)—O—, $R_{12}$ is branched $C_4$–$C_{20}$alkyl. These compounds are described in GB Patent Specification 2172284A.

h) Compounds having the formula:

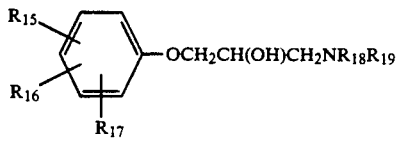

in which $R_{15}$, $R_{16}$, $R_{17}$ are, independently, hydrogen, $C_1$–$C_{15}$alkyl, $C_5$–$C_{12}$cycloalkyl, $C_6$–$C_{15}$aryl or $C_7$–$C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each —$CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are:

Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are:

Polymethacrylates, alkylated naphthalene derivatives.

Examples of dispersants/detergents are:

Polybutenylsuccinic acid-amides or -imides, polybutenyl-phosphonic acid derivatives, basic magnesium-, calcium-, and bariumsulfonates and -phenolates.

Examples of anti-wear additives and extreme pressure additives are:

Sulphur- and/or phosphorus- and/or halogen-containing compounds e.g. sulphurised vegetable oils, zinc dialkyldithiophosphates, tritolylphosphate, chlorinated paraffins, alkyl-and aryldi- and trisulphides, triphenylphosphorothionate.

The following examples are presented for the purpose of illustration only and are not to be construed to limit the nature or scope of the instant invention in any manner whatsoever.

EXAMPLE 1

2-[(2-Hydroxyethyl)amino]-4,6-bis[N-(1-cyclohexyloxy-2,2,6,6-tetramethylpiperdin-4-yl)butylamino]-1,3,5-triazine A mixture of 10.0 g (13.6 mmol) of 2-chloro-4,6-bis[N-(1-cyclohexyloxy-2,2,6,6-tetramethylpiperdin-4-yl)butylamino]-1,3,5-triazine, 3.3 g (54.6 mmol) of ethanolamine and 30 ml of dioxane is heated at reflux for four hours. The reaction mixture is then poured into 200 ml of saturated aqueous sodium bicarbonate solution. A precipitate forms. The supernatant liquid is decanted, and the precipitate is partitioned between ether (250 ml) and saturated aqueous sodium bicarbonate solution (100 ml). The ether layer is dried over anhydrous magnesium sulfate and evaporated to obtain a glassy material. Purification by flash chromatography on silica gel (4:1 heptane:ethyl acetate) affords 9.0 g (87% yield) of the title compound as a colorless glass.

Analysis: Calcd. for $C_{43}H_{80}N_8O_3$: C, 68.2; H, 10.6; N, 14.8. Found: C, 67.6; H, 10.7; N, 14.7.

EXAMPLE 2

2-[(2-Hydroxyethyl)amino]-4,6-bis[N-(1-octyloxy-2,2,6,6-tetramethylpiperidin-4-yl)butylamino]-1,3,5-triazine The title compound, a colorless glass, is prepared from the reaction of 2-chloro-4,6-bis[N-(1-octyloxy-2,2,6,6-tetramethylpiperidin-4-yl)butylamino]-1,3,5-triazine and ethanolamine according to the procedure of Example 1.

Analysis: Calcd. for $C_{47}H_{92}N_8O_3$: C, 69.1; H, 11.3; N, 13.7. Found: C, 68.2; H, 11.8; N, 13.5.

EXAMPLE 3

2-[(2-Hydroxyethyl)amino]-4,6-bis[N-(1-methoxy-2,2,6,6-tetramethylpiperidin-4-yl)butylamino]-1,3,5-triazine The title compound is prepared from the reaction of 2-chloro-4,6-bis[N-(1-methoxy-2,2,6,6-tetramethylpiperidin-4-yl)butylamino]-1,3,5-triazine and ethanolamine according to the procedure of Example 1.

EXAMPLE 4

2-[Bis(2-hydroxyethyl)amino]-4,6-bis[N-(1-cyclohexyloxy-2,2,6,6-tetramethylpiperidin-4-yl)butylamino]-1,3,5-triazine The title compound is prepared from the reaction of 2-chloro-4,6-bis[N-(1-cyclohexyloxy-2,2,6,6-tetramethylpiperidin-4-yl)butylamino]-1,3,5-triazine and diethanolamine according to the procedure of Example 1.

EXAMPLE 5

2-[Bis(2-hydroxyethyl)amino]-4,6-bis[N-(1-octyloxy-2,2,6,6-tetramethylpiperidin-4-yl)butylamino]-1,3,5-triazine The title compound is a yellow oil and is prepared from the reaction of 2-chloro-4,6-bis[N-(1-octyloxy-2,2,6,6-tetramethylpiperidin-4-yl)butylamino]-1,3,5-triazine and diethanolamine according to the procedure of Example 1.

Analysis: Calcd. for $C_{49}H_{96}N_8O_4$: C, 68.3; H, 11.2; N, 13.0. Found: C, 68.3; H, 11.9; N, 13.6.

EXAMPLE 6

2-[Bis(2-hydroxyethyl)amino]-4,6-bis[N-(1-methoxy-2,2,6,6-tetramethylpiperidin-4-yl)butylamino]-1,3,5-triazine The title compound is prepared from the reaction of 2-chloro-4,6-bis[N-(1-methoxy-2,2,6,6-tetramethylpiperidin-4-yl)butylamino]-1,3,5-triazine and diethanolamine according to the procedure of Example 1.

EXAMPLE 7

N,N'-Bis{2-[(2-hydroxyethyl)amino]-4-[N-(1-cyclohexyloxy-2,2,6,6-tetramethylpiperidin-4-yl)butylamino]-1,3,5-triazin-6-yl}-1,6-hexanediamine The title compound is prepared from the reaction of N,N'-bis{2-chloro-4-[N-(1-cyclohexyloxy-2,2,6,6-tetramethylpiperidin-4-yl)butylamino]-1,3,5-triazin-6-yl}-1,6-hexanediamine and ethanolamine.

EXAMPLE 8

N,N'-Bis{2-[(2-hydroxyethyl)amino]-4-[N-(1-octyloxy-2,2,6,6-tetramethylpiperidin-4-yl)butylamino]-1,3,5-triazin-6-yl}-1,6-hexanediamine The title compound is prepared from the reaction of N,N'-bis{2-chloro-4-[N-(1-octyloxy-2,2,6,6-tetramethylpiperidin-4-yl)butylamino]-1,3,5-triazin-6-yl}-1,6-hexanediamine and ethanolamine.

EXAMPLE 9

N,N'-Bis{2-[(2-hydroxyethyl)amino]-4-[N-(1-methoxy-2,2,6,6-tetramethylpiperidin-4-yl)butylamino]-1,3,5-triazin-6-yl}-1,6-hexanediamine The title compound is prepared from the reaction of N,N'-bis{2-chloro-4-[N-(1-methoxy-2,2,6,6-tetramethylpiperidin-4-yl)butylamino]-1,3,5-triazin-6-yl}-1,6-hexanediamine and ethanolamine.

EXAMPLE 10

N,N'-Bis(1-cyclohexyloxy-2,2,6,6-tetramethylpiperidin-4-yl)-N,N'-bis{2-[(2-hydroxyethyl)amino]-4-[N-(1-cyclohexyloxy-2,2,6,6-tetramethylpiperidin-4-yl)butylamino]-1,3,5-triazin-6-yl}-1,6-hexanediamine The title compound is prepared from the reaction of N,N'-bis(1-cyclohexyloxy-2,2,6,6-tetramethylpiperidin-4-yl)-N,N'-bis{2-chloro-4-[N-(1-cyclohexyloxy-2,2,6,6-tetramethylpiperidin-4-yl)butylamino]-1,3,5-triazin-6-yl}-1,6-hexanediamine and ethanolamine.

EXAMPLE 11

N,N'-Bis(1-octyloxy-2,2,6,6-tetramethylpiperidin-4-yl)-N,N'-bis{2-[(2-hydroxyethyl)-amino]-4-[N-(1-octyloxy-2,2,6,6-tetramethylpiperidin-4-yl)butylamino]-1,3,5-triazin-6-yl}-1,6-hexanediamine The title compound is prepared from the reaction of N,N'-bis(1-octyloxy-2,2,6,6-tetramethylpiperidin-4-yl)-N,N'-bis{2-chloro-4-[N-(1-octyloxy-2,2,6,6-tetramethylpiperidin-4-yl)butylamino]-1,3,5-triazin-6-yl}-1,6-hexanediamine and ethanolamine.

EXAMPLE 12

N,N'-Bis(1-methoxy-2,2,6,6-tetramethylpiperidin-4-yl)-N,N'-bis{2-[(2-hydroxyethyl)-amino]-4-[N-(1-methoxy-2,2,6,6-tetramethylpiperidin-4yl)butylamino]-1,3,5-triazin-6-yl}-1,6-hexanediamine The title compound is prepared from the reaction of N,N'-bis(1-methoxy-2,2,6,6-tetramethylpiperidin-4-yl)-N,N'-bis{2-chloro-4-[N-(1-methoxy-2,2,6,6-tetramethylpiperidin-4-yl)butylamino]-1,3,5-triazin-6-yl}-1,6-hexanediamine and ethanolamine.

EXAMPLE 13

2-[(2-Hydroxyethyl)amino]-4,6-bis[(1-cyclohexyloxy-2,2,6,6-tetramethylpiperidin-4-yl)oxy]-1,3,5-triazine The title compound is prepared from the reaction of 2-chloro-4,6-bis[(1-cyclohexyloxy-2,2,6,6-tetramethylpiperidin-4-yl)oxy]-1,3,5-triazine with ethanolamine.

EXAMPLE 14

2-[(2-Hydroxyethyl)amino]-4,6-bis[(1-octyloxy-2,2,6,6-tetramethylpiperidin-4-yl)oxy]-1,3,5-triazine The title compound is prepared from the reaction of 2-chloro-4,6-bis[(1-octyloxy-2,2,6,6-tetramethylpiperidin-4-yl)oxy]-1,3,5-triazine with ethanolamine.

EXAMPLE 15

N-{4,6-Bis[(1-cyclohexyloxy-2,2,6,6-tetramethylpiperidin-4-yl)butylamino]-1,3,5-triazin-2-yl}-6-aminohexanoic acid A mixture of 20.0 g (27.3 mmol) of 2-chloro-4,6-bis[N-(1-cyclohexyloxy-2,2,6,6-tetramethylpiperidin-4-yl)butylamino]-1,3,5-triazine, 25.1 g (0.164 mol) of sodium 6-aminohexanoate, and 200 ml of diglyme is heated at 140° C. for seven hours. The reaction mixture is partitioned between 1N HCl (500 ml) and ether (400 ml), and the aqueous phase is extracted with ether (200 ml). The combined organic layers are washed with water (2×200 ml) and saturated aqueous sodium chloride solution (200 ml), and then dried over anhydrous magnesium sulfate, and finally concentrated to obtain a glass. Purification by flash chromatography on silica gel (2:1 heptane:ethyl acetate) affords 15.7 g (69% yield) of the title compound as a white powdery glass.

Analysis:

Calcd. for $C_{47}H_{86}N_8O_4$: C, 68.2; H, 10.5; N, 13.6. Found: C, 68.0; H, 10.8; N, 13.5.

EXAMPLE 16

N-{4,6-Bis[(1-octyloxy-2,2,6,6-tetramethylpiperidin-4-yl)butylamino]-1,3,5-triazin-2-yl}-6-aminohexanoic acid The title compound, a colorless glass, is prepared from 2-chloro-4,6-bis[N-(1-octyloxy-2,2,6,6-tetramethylpiperidin-4-yl)butylamino]-1,3,5-triazine and sodium 6-aminohexanoate according to the procedure of Example 15.

Analysis: Calcd. for $C_{51}H_{98}N_8O_4$: C, 69.0; H, 11.1; N, 12.6. Found: C, 69.0; H, 11.6; N, 12.5.

EXAMPLE 17

N-{4,6-Bis[(1-methoxy-2,2,6,6-tetramethylpiperidin-4-yl)butylamino]-1,3,5-triazin-2-yl}-6-aminohexanoic acid The title compound is prepared from 2-chloro-4,6-bis[N-(1-methoxy-2,2,6,6-tetramethylpiperidin-4-yl)butylamino]-1,3,5-triazine and sodium 6-aminohexanoate according to the procedure of Example 15.

EXAMPLE 18

N,N'-Bis(1-cyclohexyloxy-2,2,6,6-tetramethylpiperidin-4-yl)-N,N'-bis{2-[(5-carboxypentyl)amino]-4-[N-(1-cyclohexyloxy-2,2,6,6-tetramethylpiperidin-4-yl)butylamino]-1,3,5-triazin-6-yl}-1,6-hexanediamine The title compound is prepared from the reaction of N,N'-bis(1-cyclohexyloxy-2,2,6,6-tetramethylpiperidin-4-yl)-N,N'-bis{2-chloro-4-[N-(1-cyclohexyloxy-2,2,6,6-tetramethylpiperidin-4-yl)butylamino]-1,3,5-triazin-6-yl}-1,6-hexanediamine and sodium 6-aminohexanoate.

EXAMPLE 19

N,N'-Bis(1-octyloxy-2,2,6,6-tetramethylpiperidin-4-yl)-N,N'-bis{2-[(5-carboxypentyl)amino]-4-[N-(1-octyloxy-2,2,6,6-tetramethylpiperidin-4-yl)butylamino]-1,3,5-triazin-6-yl}-1,6-hexanediamine The title compound is prepared from the reaction of N,N'-bis(1-octyloxy-2,2,6,6-tetramethylpiperidin-4-yl)-N,N'-bis{2-chloro-4-[N-(1-octyloxy-2,2,6,6-tetramethylpiperidin-4-yl)butylamino]-1,3,5-triazin-6-yl}-1,6-hexanediamine and sodium 6-aminohexanoate.

EXAMPLE 20

2-Amino-4,6-bis[N-(1-methoxy-2,2,6,6-tetramethylpiperidin-4-yl)butylamino]-1,3,5-triazine A mixture of 13.0 g (78.8 mmol) of 2-amino-4,6-dichloro-1,3,5-triazine, 39.6 g (164 mmol) of 4-(butylamino)-1-methoxy-2,2,6,6-tetramethylpiperidine, 6.6 g (165 mmol) of sodium hydroxide, and 200 ml of xylene is heated at reflux for seven hours. A Dean-Stark trap is used to remove water from the reaction. The reaction mixture is diluted with ethyl acetate (200 ml) and treated with 1N HCl to neutralize the sodium hydroxide. Excess acid is then neutralized with saturated sodium bicarbonate solution. The organic layer is dried over anhydrous magnesium sulfate and concentrated to obtain a gummy residue. Crystallization of the residue from acetonitrile and recrystallization from methanol affords 24.6 g (54% yield) of the title compound as a white solid melting at 163°–65° C.

Analysis: Calcd. for $C_{31}H_{60}N_8O_2$: C, 64.5; H, 10.5; N, 19.4. Found: C, 64.3; H, 10.7; N, 19.4.

EXAMPLE 21

2-Amino-4,6-bis[N-(1-octyloxy-2,2,6,6-tetramethylpiperidin-4-yl)butylamino]-1,3,5-triazine The title compound is prepared from 2-amino-4,6-dichloro-1,3,5-triazine and 4-(butylamino)-1-octyloxy-2,2,6,6-tetramethylpiperidine according to the procedure of Example 20.

EXAMPLE 22

2-Amino-4,6-bis[N-(1-cyclohexyloxy-2,2,6,6-tetramethylpiperidin-4-yl)butylamino]-1,3,5-triazine The title compound is prepared from 2-amino-4,6-dichloro-1,3,5-triazine and 4-(butylamino)-1-cyclohexyloxy-2,2,6,6-tetramethylpiperidine according to the procedure of Example 20.

EXAMPLE 23

N-{4,6-Bis[N-(1-cyclohexyloxy-2,2,6,6-tetramethylpiperidin-4-yl)butylamino]-1,3,5-triazin-2-yl}succinamic acid The title compound is prepared from the reaction of succinic anhydride with the compound made in Example 22.

EXAMPLE 24

N-{4,6-Bis[N-(1-octyloxy-2,2,6,6-tetramethylpiperidin-4-yl)butylamino]-1,3,5-triazin-2-yl}succinamic acid The title compound is prepared from the reaction of succinic anhydride with the compound made in Example 21.

EXAMPLE 25

N-{4,6-Bis[N-(1-methoxy-2,2,6,6-tetramethylpiperidin-4-yl)butylamino]-1,3,5-triazin-2-yl}succinamic acid The title compound is prepared from the reaction of succinic anhydride with the compound made in Example 20.

EXAMPLE 26

2-{[(2-Hydroxy-3-butoxy)propyl]amino}-4,6-bis[N-(1-cyclohexyloxy-2,2,6,6-tetramethylpiperidin-4-yl)butylamino]-1,3,5-triazine The title compound is prepared from the reaction of butyl glycidyl ether with the compound made in Example 22.

EXAMPLE 27

2-{[(2-Hydroxy-3-butoxy)propyl]amino}-4,6-bis[N-(1-octyloxy-2,2,6,6-tetramethylpiperidin-4-yl)butylamino]-1,3,5-triazine The title compound is prepared from the reaction of butyl glycidyl ether with the compound made in Example 21.

EXAMPLE 28

4,6-Bis[N-(1-cyclohexyloxy-2,2,6,6-tetramethylpiperidin-4-yl)butylamino]-1,3,5-triazin-2-yl isocyanate The title compound is prepared from the reaction of oxalyl chloride with the compound prepared in Example 22.

EXAMPLE 29

4,6-Bis[N-(1-octyloxy-2,2,6,6-tetramethylpiperidin-4-yl)butylamino]-1,3,5-triazin-2-yl isocyanate The title compound is prepared from the reaction of oxalyl chloride with the compound prepared in Example 21.

EXAMPLE 30

4,6-Bis[N-(1-methoxy-2,2,6,6-tetramethylpiperidin-4-yl)butylamino]-1,3,5-triazin-2-yl isocyanate The title compound is prepared from the reaction of oxalyl chloride with the compound prepared in Example 20.

EXAMPLE 31

2-(Oxiranylmethoxy)-4,6-bis[N-(1-methoxy-2,2,6,6-tetramethylpiperidin-4-yl)butylamino]-1,3,5-triazine The title compound is prepared by the reaction of 2-chloro-4,6-bis[N-(1-methoxy-2,2,6,6-tetramethylpiperidin-4-yl)-butylamino]-1,3,5-triazine with sodium hydroxide and 3-chloro-1,2-propanediol.

EXAMPLE 32

2-(Oxiranylmethoxy)-4,6-bis[N-(1-octyloxy-2,2,6,6-tetramethylpiperidin-4-yl)butylamino]-1,3,5-triazine The title compound is prepared by the reaction of 2-chloro-4,6-bis[N-(1-octyloxy-2,2,6,6-tetramethylpiperidin-4-yl)butylamino]-1,3,5-triazine with sodium hydroxide and 3-chloro-1,2-propanediol.

EXAMPLE 33

2-(Oxiranylmethoxy)-4,6-bis[N-(1-cyclohexyloxy-2,2,6,6-tetramethylpiperidin-4-yl)butylamino]-1,3,5-triazine The title compound is prepared by the reaction of 2-chloro-4,6-bis[N-(1-cyclohexyloxy-2,2,6,6-tetramethylpiperidin-4-yl)butylamino]-1,3,5-triazine with sodium hydroxide and 3-chloro-1,2-propanediol.

EXAMPLE 34

2-[Bis(methoxymethyl)amino]-4,6-bis[N-(1-cyclohexyloxy-2,2,6,6-tetramethylpiperidin-4-yl)butylamino]-1,3,5-triazine The title compound is prepared from the reaction of the compound prepared in Example 22 with formaldehyde, methanol, and mineral acid.

EXAMPLE 35

2-[Bis(methoxymethyl)amino]-4,6-bis[N-(1-octyloxy-2,2,6,6-tetramethylpiperidin-4-yl)butylamino]-1,3,5-triazine The title compound is prepared from the reaction of the compound prepared in Example 21 with formaldehyde, methanol, and mineral acid.

EXAMPLE 36

2-[Bis(methoxymethyl)amino]-4,6-bis[N-(1-methoxy-2,2,6,6-tetramethylpiperidin-4-yl)butylamino]-1,3,5-triazine The title compound, a colorless glass, is prepared from the reaction of the compound prepared in Example 20 with formaldehyde, methanol, and sulfuric acid.

Analysis: Calcd. for $C_{35}H_{68}N_8O_4$: C, 63.2; H, 10.3; N, 16.9. Found: C, 64.1; H, 10.7; N, 16.1.

EXAMPLE 37

2-[(2-Hydroxypropyl)amino]-4,6-bis[N-(1-methoxy-2,2,6,6-tetramethylpiperidin-4-yl)butylamino]-1,3,5-triazine The title compound is prepared from the reaction of the compound prepared in Example 20 with propylene oxide.

EXAMPLE 38

2-[(2-Hydroxypropyl)amino]-4,6-bis[N-(1-octyloxy-2,2,6,6-tetramethylpiperidin-4-yl)butylamino]-1,3,5-triazine The title compound is prepared from the reaction of the compound prepared in Example 21 with propylene oxide.

EXAMPLE 39

2-[(2-Hydroxypropyl)amino]-4,6-bis[N-(1-cyclohexyloxy-2,2,6,6-tetramethylpiperidin-4-yl)butylamino]-1,3,5-triazine The title compound is prepared from the reaction of the compound prepared in Example 22 with propylene oxide.

EXAMPLE 40

2-[N-(2-Hydroxyethyl)-N-(1-cyclohexyloxy-2,2,6,6-piperidin-4-yl)amino]-4,6-bis[N-(1-cyclohexyloxy-2,2,6,6-tetramethylpiperidin-4-yl)butylamino]-1,3,5-triazine The title compound is prepared by the reaction of 2-chloro-4,6-bis[N-(1-cyclohexyloxy-2,2,6,6-tetramethylpiperidin-4-yl)butylamino]-1,3,5-triazine with 4-[(2-hydroxyethyl)amino]-1-cyclohexyloxy-2,2,6,6-tetramethylpiperidine.

EXAMPLE 41

2-[N-(2-Hydroxyethyl)-N-(1-octyloxy-2,2,6,6-piperidin-4-yl)amino]-4,6-bis[N-(1-octyloxy-2,2,6,6-tetramethylpiperidin-4-yl)butylamino]-1,3,5-triazine The title compound is prepared by the reaction of 2-chloro-4,6-bis[N-(1-octyloxy-2,2,6,6-tetramethylpiperidin-4-yl)-butylamino]-1,3,5-triazine with 4-[(2-hydroxyethyl)amino]-1-octyloxy-2,2,6,6-tetramethylpiperidine.

EXAMPLE 42

2-[N-(2-Hydroxyethyl)-N-(1-methoxy-2,2,6,6-piperidin-4-yl)amino]-4,6-bis[N-(1-methoxy-2,2,6,6-tetramethylpiperidin-4-yl)butylamino]-1,3,5-triazine The title compound is prepared by the reaction of 2-chloro-4,6-bis[N-(1-methoxy-2,2,6,6-tetramethylpiperidin-4-yl)-butylamino]-1,3,5-triazine with 4-[(2-hydroxyethyl)amino]-1-methoxy-2,2,6,6-tetramethylpiperidine.

EXAMPLE 43

N-{4,6-Bis[N-(1-cyclohexyloxy-2,2,6,6-tetramethylpiperidin-4-yl)butylamino]-1,3,5-triazin-2-yl}glycine The title compound is prepared from the reaction of 2-chloro-4,6-bis[N-(1-cyclohexyloxy-2,2,6,6-tetramethylpiperidin-4-yl)butylamino]-1,3,5-triazine and glycine according to the procedure of Example 15.

EXAMPLE 44

N-{4,6-Bis[N-(1-cyclohexyloxy-2,2,6,6-tetramethylpiperidin-4-yl)butylamino]-1,3,5-triazin-2-yl}-β-alanine The title compound is prepared from the reaction of 2-chloro-4,6-bis[N-(1-cyclohexyloxy-2,2,6,6-tetramethylpiperidin-4-yl)butylamino]-1,3,5-triazine and β-alanine according to the procedure of Example 15.

EXAMPLE 45

N-{4,6-Bis[N-(1-octyloxy-2,2,6,6-tetramethylpiperidin-4-yl)butylamino]-1,3,5-triazin-2-yl}glycine The title compound is prepared from the reaction of 2-chloro-4,6-bis[N-(1-octyloxy-2,2,6,6-tetramethylpiperidin-4-yl)butylamino]-1,3,5-triazine and glycine according to the procedure of Example 15.

EXAMPLE 46

N-{4,6-Bis[N-(1-octyloxy-2,2,6,6-tetramethylpiperidin-4-yl)butylamino]-1,3,5-triazin-2-yl}-β-alanine The title compound is prepared from the reaction of 2-chloro-4,6-bis[N-(1-octyloxy-2,2,6,6-tetramethylpiperidin-4-yl)butylamino]-1,3,5-triazine and β-alanine according to the procedure of Example 15.

EXAMPLE 47

N-{4,6-Bis[N-(1-methoxy-2,2,6,6-tetramethylpiperidin-4-yl)butylamino]-1,3,5-triazin-2-yl}glycine The title compound is prepared from the reaction of 2-chloro-4,6-bis[N-(1-methoxy-2,2,6,6-tetramethylpiperidin-4-yl)butylamino]-1,3,5-triazine and glycine according to the procedure of Example 15.

EXAMPLE 48

N-{2,4-Bis[N-(1-methoxy-2,2,6,6-tetramethylpiperidin-4-yl)butylamino]-1,3,5-triazin-6-yl}-β-alanine The title compound is prepared from the reaction of 2-chloro-4,6-bis[N-(1-methoxy-2,2,6,6-tetramethylpiperidin-4-yl)butylamino]-1,3,5-triazine and β-alanine according to the procedure of Example 15.

EXAMPLE 49

{2,4-Bis[N-(1-octyloxy-2,2,6,6-tetramethylpiperidin-4-yl)butylamino]-1,3,5-triazin-6-yl}hydrazine The title compound is prepared from the reaction of 2-chloro-4,6-bis[N-(1-octyloxy-2,2,6,6-tetramethylpiperidin-4-yl)butylamino]-1,3,5-triazine and hydrazine.

EXAMPLE 50

2-[(2-Hydroxyethyl)amino]-4,6-bis[N-(1-octadecyloxy-2,2,6,6-tetramethylpiperidin-4-yl)butylamino]-1,3,5-triazine The title compound is prepared from the reaction of 2-chloro-4,6-bis[N-(1-octadecyloxy-2,2,6,6-tetramethylpiperidin-4-yl)butylamino]-1,3,5-triazine and ethanolamine according to the procedure of Example 1.

EXAMPLE 51

2-[(2-Hydroxyethyl)amino-4,6-bis{N-[1-(α-methylbenzyloxy)-2,2,6,6-tetramethylpiperidin-4-yl]butylamino}-1,3,5-triazine The title compound is prepared from the reaction of 2-chloro-4,6-bis{N-[1-(α-methylbenzyloxy)-2,2,6,6-tetramethylpiperidin-4-yl]butylamino}-1,3,5-triazine and ethanolamine according to the procedure of Example 1.

EXAMPLE 52

2,2-Bis{4-[[2-[(5-carboxypentyl)amino]-4-[N-(1-cyclohexyloxy-2,2,6,6-tetramethylpiperidin-4-yl)butylamino]-1,3,5-triazin-6-yl]oxy]phenyl}propane The title compound is prepared from the reaction of 2,2-bis{4-[[2-chloro-4-[N-(1-cyclohexyloxy-2,2,6,6-tetramethylpiperidin-4-yl)butylamino]-1,3,5-triazin-6-yl]oxy]phenyl}propane with 6-aminohexanoic acid.

EXAMPLE 53

2-[(2-Hydroxyethyl)amino]-4,6-bis[N-(1-cyclohexyloxy-2,2,6,6-tetramethylpiperidin-4-yl)dodecylamino]-1,3,5-triazine The title compound is prepared from the reaction of 2-chloro-4,6-bis[N-(1-cyclohexyloxy-2,2,6,6-tetramethylpiperidin-4-yl)dodecylamino]-1,3,5-triazine with ethanolamine according to the procedure of Example 1.

EXAMPLE 54

2-[(2-Hydroxyethyl)amino]-4,6-bis[(1-cyclohexyloxy-2,2,6,6-tetramethylpiperidin-4-yl)-amino]-1,3,5-triazine The title compound is prepared from the reaction of 2-chloro-4,6-bis[(1-cyclohexyloxy-2,2,6,6-tetramethylpiperidin-4-yl)amino]-1,3,5-triazine with ethanolamine according to the procedure of Example 1.

EXAMPLE 55

2-[Bis(butoxymethyl)amino]-4,6-bis[N-(1-cyclohexyloxy-2,2,6,6-tetramethylpiperidin-4-yl)butylamino]-1,3,5-triazine The title compound is prepared from the reaction of the compound prepared in Example 22 with formaldehyde, 1-butanol, and mineral acid.

EXAMPLE 56

2-[Bis(butoxymethyl)amino]-4,6-bis[N-(1-octyloxy-2,2,6,6-tetramethylpiperidin-4-yl)butylamino]-1,3,5-triazine The title compound is prepared from the reaction of the compound prepared in Example 21 with formaldehyde, 1-butanol, and mineral acid.

EXAMPLE 57

2,4-Bis[N-(methoxymethyl)-N-(1-cyclohexyloxy-2,2,6,6-piperidin-4-yl)amino]-6-[N-(1-cyclohexyloxy-2,2,6,6-tetramethylpiperidin-4-yl)butylamino]-1,3,5-triazine The title compound is prepared from 2,4-bis[(1-cyclohexyloxy-2,2,6,6-piperidin-4-yl)-amino]-6-[N-(1-cyclohexyloxy-2,2,6,6-tetramethylpiperidin-4-yl)butylamino]-1,3,5-triazine, formaldehyde, methanol, and mineral acid.

EXAMPLE 58

2,4-Bis[N-(methoxymethyl)-N-(1-octyloxy-2,2,6,6-piperidin-4-yl)amino]-6-[N-(1-octyloxy-2,2,6,6-tetramethylpiperidin-4-yl)butylamino]-1,3,5-triazine The title compound is prepared from 2,4-bis[(1-octyloxy-2,2,6,6-piperidin-4-yl)amino]-6-[N-(1-octyloxy-2,2,6,6-tetramethylpiperidin-4-yl)butylamino]-1,3,5-triazine, formaldehyde, methanol, and mineral acid.

EXAMPLE 59

N,N'-Bis{2-[N-(methoxymethyl)-N-(1-cyclohexyloxy-2,2,6,6-tetramethylpiperidin-4-yl)amino]-4-[N-(1-cyclohexyloxy-2,2,6,6-tetramethylpiperidin-4-yl)butylamino]-1,3,5-triazin-6-yl}-1,6-hexanediamine The title compound is prepared from N,N'-bis{2-[(1-cyclohexyloxy-2,2,6,6-tetramethylpiperidin-4-yl)amino]-4-[N-(1-cyclohexyloxy-2,2,6,6-tetramethylpiperidin-4-yl)butylamino]-1,3,5-triazin-6-yl}-1,6-hexanediamine, formaldehyde, methanol, and mineral acid.

EXAMPLE 60

N,N'-Bis{2-[N-(methoxymethyl)-N-(1-octyloxy-2,2,6,6-tetramethylpiperidin-4-yl)amino]-4-[N-(1-octyloxy-2,2,6,6-tetramethylpiperidin-4-yl)butylamino]-1,3,5-triazin-6-yl}-1,6-hexanediamine The title compound is prepared from N,N'-bis{2-[(1-octyloxy-2,2,6,6-tetramethylpiperidin-4-yl)amino]-4-[N-(1-octyloxy-2,2,6,6-tetramethylpiperidin-4-yl)butylamino]-1,3,5-triazin-6-yl}-1,6-hexanediamine, formaldehyde, methanol, and mineral acid.

EXAMPLE 61

N,N'-Bis(1-cyclohexyloxy-2,2,6,6-tetramethylpiperidin-4-yl)-N,N'-bis{2-[N-(methoxymethyl)-N-(1-cyclohexyloxy-2,2,6,6-tetramethylpiperidin-4-yl)amino]-4-[N-(1-cyclohexyloxy-2,2,6,6-tetramethylpiperidin-4-yl)butylamino]-1,3,5-triazin-6-yl}-1,6-hexanediamine The title compound is prepared from N,N'-bis(1-cyclohexyloxy-2,2,6,6-tetramethylpiperidin-4-yl)-N,N'-bis{2-[(1-cyclohexyloxy-2,2,6,6-tetramethylpiperidin-4-yl)amino]-4-[N-(1-cyclohexyloxy-2,2,6,6-tetramethylpiperidin-4-yl)butylamino]-1,3,5-triazin-6-yl}-1,6-hexanediamine, formaldehyde, methanol, and mineral acid.

EXAMPLE 62

N,N'-Bis(1-octyloxy-2,2,6,6-tetramethylpiperidin-4-yl)-N,N'-bis{2-[N-(methoxymethyl)-N-(1-octyloxy-2,2,6,6-tetramethylpiperidin-4-yl)amino]-4-[N-(1-octyloxy-2,2,6,6-tetramethylpiperidin-4-yl)butylamino]-1,3,5-triazin-6-yl}-1,6-hexanediamine The title compound is prepared from N,N'-bis(1-octyloxy-2,2,6,6-tetramethylpiperidin-4-yl)-N,N'-bis{2-[(1-octyloxy-2,2,6,6-tetramethylpiperidin-4-yl)amino]-4-[N-(1-octyloxy-2,2,6,6-tetramethylpiperidin-4-yl)butylamino]-1,3,5-triazin-6-yl}-1,6-hexanediamine, formaldehyde, methanol, and mineral acid.

EXAMPLE 63

N,N'-Bis{2-isocyanato-4-[(1-cyclohexyloxy-2,2,6,6-tetramethylpiperidin-4-yl)butylamino]-1,3,5-triazin-6-yl}-1,6-hexanediamine The title compound is prepared by the reaction of N,N'-bis{2-amino-4-[N-(1-cyclohexyloxy-2,2,6,6-tetramethylpiperidin-4-yl)butylamino]-1,3,5-triazin-6-yl}-1,6-hexanediamine with oxalyl chloride.

EXAMPLE 64

N,N'-Bis{2-(oxiranylmethoxy)-4-[N-(1-cyclohexyloxy-2,2,6,6-tetramethylpiperidine-4-yl)butylamino]-1,3,5-triazin-6-yl}-1,6-hexanediamine The title compound is prepared by the reaction of N,N'-bis{2-chloro-4-[N-(1-cyclohexyloxy-2,2,6,6-tetramethylpiperidin-4-yl)butylamino]-1,3,5-triazin-6-yl}-1,6-hexanediamine with sodium hydroxide and 3-chloro-1,2-propanediol.

EXAMPLE 65

N,N'-Bis(1-cyclohexyloxy-2,2,6,6-tetramethylpiperidin-4-yl)-N,N'-bis{2-isocyanato-4-[N-(1-cyclohexyloxy-2,2,6,6-tetramethylpiperidin-4-yl)butylamino]-1,3,5-triazin-6-yl}-1,6-hexanediamine The title compound is prepared by the reaction of N,N'-bis(1-cyclohexyloxy-2,2,6,6-tetramethylpiperidin-4-yl)-N,N'-bis{2-amino-4-[N-(1-cyclohexyloxy-2,2,6,6-tetramethylpiperidin-4-yl)butylamino]-1,3,5-triazin-6-yl}-1,6-hexanediamine and oxalyl chloride.

EXAMPLE 66

N,N'-Bis(1-cyclohexyloxy-2,2,6,6-tetramethylpiperidin-4-yl)-N,N'-bis{2-(oxiranylmethoxy)-4-[N-(1-cyclohexyloxy-2,2,6,6-tetramethylpiperidin-4-yl)butylamino]-1,3,5-triazin-6-yl}-1,6-hexanediamine The title compound is prepared by the reaction of N,N'-bis(1-cyclohexyloxy-2,2,6,6-tetramethylpiperidin-4-yl)-N,N'-bis{2-chloro-4-[N-(1-cyclohexyloxy-2,2,6,6-tetramethylpiperidin-4-yl)butylamino]-1,3,5-triazin-6-yl}-1,6-hexanediamine with sodium hydroxide and 3-chloro-1,2-propanediol.

EXAMPLE 67

2,4-Bis[N-(2-hydroxyethyl)-N-(1-cyclohexyloxy-2,2,6,6-piperidin-4-yl)amino]-6-[N-(1-cyclohexyloxy-2,2,6,6-tetramethylpiperidin-4-yl)butylamino]-1,3,5-triazine The title compound is prepared by the reaction of 2,4-dichloro-6-[N-(1-cyclohexyloxy-2,2,6,6-tetramethylpiperidin-4-yl)butylamino]-1,3,5-triazine with 4-(2-hydroxyethyl)amino-1-cyclohexyloxy-2,2,6,6-tetramethylpiperidine.

EXAMPLE 68

N,N'-Bis{2-isocyanato-4-[N-(1-octyloxy-2,2,6,6-tetramethylpiperidin-4-yl)butylamino]-1,3,5-triazin-6-yl}-1,6-hexanediamine The title compound is prepared by the reaction of N,N'-bis{2-amino-4-[N-(1-octyloxy-2,2,6,6-tetramethylpiperidin-4-yl)butylamino]-1,3,5-triazin-6-yl}-1,6-hexanediamine with oxalyl chloride.

EXAMPLE 69

N,N'-Bis{2-(oxiranylmethoxy)-4-[N-(1-octyloxy-2,2,6,6-tetramethylpiperidin-4-yl)butylamino]-1,3,5-triazin-6-yl}-1,6-hexanediamine The title compound is prepared by the reaction of N,N'-bis{2-chloro-4-[N-(1-octyloxy-2,2,6,6-tetramethylpiperidin-4-yl)butylamino]-1,3,5-triazin-6-yl}-1,6-hexanediamine with sodium hydroxide and 3-chloro-1,2-propanediol.

EXAMPLE 70

N,N'-Bis(1-octyloxy-2,2,6,6-tetramethylpiperidin-4-yl)-N,N'-bis{2-isocyanato-4-[N-(1-octyloxy-2,2,6,6-tetramethylpiperidin-4-yl)butylamino]-1,3,5-triazin-6-yl}-1,6-hexanediamine The title compound is prepared by the reaction of N,N'-bis(1-octyloxy-2,2,6,6-tetramethylpiperidin-4-yl)-N,N'-bis{2-amino-4-[N-(1-octyloxy-2,2,6,6-tetramethylpiperidin-4-yl)butylamino]-1,3,5-triazin-6-yl}-1,6-hexanediamine and oxalyl chloride.

EXAMPLE 71

N,N'-Bis(1-octyloxy-2,2,6,6-tetramethylpiperidin-4-yl)-N,N'-bis{2-(oxiranylmethoxy)-4-[N-(1-octyloxy-2,2,6,6-tetramethylpiperidin-4-yl)butylamino]-1,3,5-triazin-6-yl}-1,6-hexanediamine The title compound is prepared by the reaction of N,N'-bis(1-octyloxy-2,2,6,6-tetramethylpiperidin-4-yl)-N,N'-bis{2-chloro-4-[N-(1-octyloxy-2,2,6,6-tetramethylpiperidin-4-yl)butylamino]-1,3,5-triazin-6-yl}-1,6-hexanediamine with sodium hydroxide and 3-chloro-1,2-propanediol.

EXAMPLE 72

2,4-Bis[N-(2-hydroxyethyl)-N-(1-octyloxy-2,2,6,6-piperidin-4-yl)amino]-6-[N-(1-octyloxy-2,2,6,6-tetramethylpiperidin-4-yl)butylamino]-1,3,5-triazine The title compound is prepared by the reaction of 2,4-dichloro-6-[N-(1-octyloxy-2,2,6,6-tetramethylpiperidin-4-yl)butylamino]-1,3,5-triazine with 4-(2-hydroxyethyl)amino-1-octyloxy-2,2,6,6-tetramethylpiperidine.

EXAMPLE 73

When 2-amino-4,6-bis[N-(1-cyclohexyloxy-2,2,6,6-tetramethylpiperidin-4-yl)butylamino]-1,3,5-triazine is reacted with Araldite DY027 (a mixture of $C_8$-$C_{10}$ glycidyl ethers), a mixture of 2-hydroxypropyl $C_8$-$C_{10}$ ethers analogous to the compound prepared in Example 26 is obtained.

EXAMPLE 74

When 2-amino-4,6-bis[N-(1-octyloxy-2,2,6,6-tetramethylpiperidin-4-yl)butylamino]-1,3,5-triazine is reacted with Araldite DY027 (a mixture of $C_8$-$C_{10}$ glycidyl ethers), a mixture of 2-hydroxypropyl $C_8$-$C_{10}$ ethers analogous to the compound prepared in Example 27 is obtained.

EXAMPLE 75

A polyester polyurethane refinish enamel is prepared from a polyester resin (DESMOPHEN® 670A-80, Mobay) and a polyurethane resin (DESMODUR® N-75, Mobay) in a ratio of 1/0.1/1 equivalents, with 1% DABCO® T-12(1,4-diazabicyclo[2.2.2]octane, Air Products) as catalyst. The enamel is stabilized with 2% by weight, based on resin solids, of various hindered amine stabilizers. The stabilized enamel is spray applied to a thickness of 1.8-2.0 mils (0.0457-0.0508 mm) onto glass plates and baked for 30 minutes at 140° F. (60° C.). After storage for one month in an air-conditioned room, the films are removed from the glass plates and placed in a round-bottomed flask and then extracted with refluxing toluene for one hour. The films are then removed and the toluene is analyzed for any stabilizer extracted by gas chromatography.

If the stabilizer is chemically bonded to the polymer film, little if any of the stabilizer is extracted by the refluxing toluene.

| Compound of Example | Percent Stabilizer Extracted |
|---|---|
| HA 1* | 100 |
| 1 | 0 |
| 2 | 0 |
| 15 | 23 |
| 16 | 21 |

*HA 1 is bis(1-octyloxy-2,2,6,6-tetramethylpiperidin-4-yl) sebacate.

The instant reactable stabilizers are chemically bonded to the polymer film and resist extraction whereas a non-reactable hindered amine is not chemically bonded to the polymer and is extracted totally.

EXAMPLE 76

The coated glass plates prepared in Example 75 are placed in an oven at 140° F. (60° C.) for 49 days. The plates are then removed and inspected for any signs of haziness or incompatibility.

| Compound of Example | Appearance |
|---|---|
| HA 1* | cloudy |
| 1 | clear |
| 2 | clear |
| 15 | clear |
| 16 | clear |

*HA 1 is bis(1-octyloxy-2,2,6,6-tetramethylpiperidin-4-yl) sebacate.

The instant stabilizers which are chemically bonded to the polymer film do not cause any haze or incompatibility problems in contrast to a non-reactable hindered amine stabilizer where cloudiness develops in its presence.

EXAMPLE 77

The enamel prepared in Example 75 is spray applied to a thickness of 1.8-2.0 mils (0.0457-0.0508 mm) onto 6"×6" (15.24 cm×15.24 cm) XENOY® (polycarbonate, General Electric) panels and force dried for 30 minutes at 140° F. (60° C.). After storage for one month in an air-conditioned room, the XENOY® panels are placed in a jar with 20 ml of distilled water. The jars are then placed in an oven at 140° F. (60° C.). After 40 days, the jars are removed and the coated panels are tested for adhesion of the enamel coating thereon according to ASTM D-3359.

| Compound of Example | Percent Coating Removed |
|---|---|
| HA 2* | 85 |
| 1 | 0 |
| 2 | 0 |

*HA 2 is bis(1,2,2,6,6-pentamethylpiperidin-4-yl) sebacate.

The coatings containing the reactable instant compounds maintained their adherence to the substrate while the coating containing a non-reactable stabilizer is less resistant to delamination.

EXAMPLE 78

A model high solids thermoset acrylic enamel based on a binder of 60% of a polymer comprising monomers such as 2-hydroxyethyl acrylate, butyl acrylate, butyl methacrylate, styrene and acrylic acid, and 40% of a melamine resin with an acid catalyst such as p-toluenesulfonic acid is formulated and stabilized with 1% by weight, based on resin solids, of a variety of hindered amine stabilizers.

This enamel is spray applied to a thickness of 1.8-2.0 mils (0.0457-0.0508 mm) onto glass plates and baked for 30 minutes at 250° F. (121° C.). After storage for one week in an air-conditioned room, the films are removed from the glass plates and placed in a round-bottomed flask and extracted with refluxing toluene for one hour. After one hour, the films are removed and the toluene extract is analyzed for extracted stabilizer by gas chromatography.

| Compound of Example | Percent Stabilizer Extracted |
|---|---|
| HA 1* | 100 |
| 1 | 0 |
| 2 | 0 |

*HA 1 is bis(1-octyloxy-2,2,6,6-tetramethylpiperidin-4-yl) sebacate.

The reactable stabilizers of instant Examples 1 and 2 resist extraction from the stabilized enamel whereas the non-reactable stabilizer is totally extracted.

EXAMPLE 79

The enamel prepared in Example 78 is also spray applied onto cold rolled steel to a thickness of 1.8-2.0 mils (0.0457-0.0508 mm) and baked for 30 minutes at 250° F. (121° C.). After storage for one week in an air-conditioned room, the Knoop hardness of the cured films is determined.

| Compound of Example | Knoop Hardness |
| --- | --- |
| unstabilized | 11.3 |
| 1 | 11.7 |
| 2 | 11.8 |

The effectiveness of cure is ascertained from the Knoop hardness values. The higher numbers indicate greater hardness and better cure. The instant compounds do not interfere with the acid catalyzed cure of the thermoset acrylic resin.

EXAMPLE 80

2-Chloro-4,6-bis[N-(1-cyclohexyloxy-2,2,6,6-tetramethylpiperidin-4-yl)butylamino]-s-triazine A mixture of 57.7 g (0.448 mol) of 70% aqueous tert-butyl hydroperoxide, 250 ml of cyclohexane and 100 ml of saturated sodium chloride solution is agitated vigorously and the organic layer is then separated and dried over anhydrous magnesium sulfate. The drying agent is removed by filtration. The filtrate, 30.0 g (0.056 mol) of 2-chloro-4,6-bis[N-(2,2,6,6-tetramethylpiperidin-4-yl)butylamino]-s-triazine and 1.0 g of molybdenum trioxide are placed in a pressure bottle and heated at 130°-140° C. The reaction mixture quickly turns red and heating is continued till the red color is discharged. The reaction mixture is allowed to cool and solids are removed by filtration. The filtrate is concentrated under reduced pressure to give an oil which is purified by flash chromatography on silica gel to afford 30.3 g. (74% yield) of the title compound as a white glass.

EXAMPLE 81

2-Chloro-4,6-bis[N-(1-octyloxy-2,2,6,6-tetramethylpiperidin-4-yl)butylamino]-s-triazine A mixture of 57.7 g (0.448 mol) of 70% aqueous tert-butyl hydroperoxide, 340 ml of octane, and 50 ml of saturated sodium chloride solution is agitated vigorously, and the organic layer is then separated and dried over anhydrous magnesium sulfate. The drying agent is removed by filtration. One-half of the tert-butyl hydroperoxide/octane solution is combined with 30.0 g (0.056 mol) of molybdenum trioxide and the mixture is heated at reflux. Water is collected in a Dean-Stark trap. Once the mixture turns red, the remaining tert-butyl hydroperoxide/octane solution is added over a three-hour period while the reaction mixture is maintained at reflux. The mixture is heated for an additional hour to discharge the red color. The reaction mixture is then cooled to room temperature and solids are removed by filtration. The filtrate is concentrated under reduced pressure to obtain an amber oil which is purified by flash chromatography on silica gel (40:1, heptane/ethyl acetate) to afford 32.7 g (74% yield) of the title compound as a colorless syrup.

What is claimed is:

1. A composition stabilized against the deleterious effects of heat, oxygen and actinic light which comprises
   (a) a synthetic polymer, and
   (b) an effective stabilizing amount of a compound of the formula I, II, III, IV, V, VI, VII, VIII, IX, X or XI

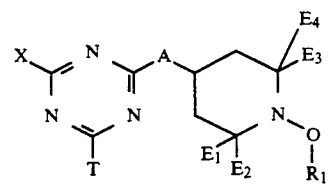

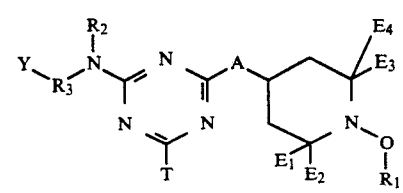

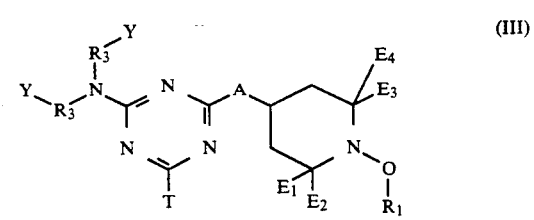

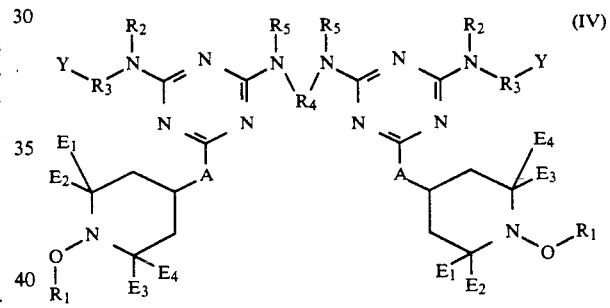

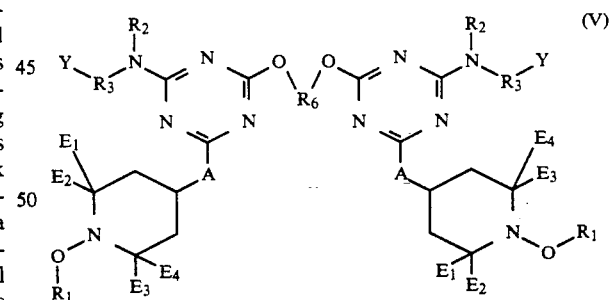

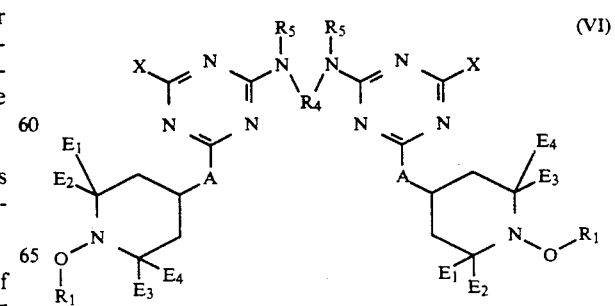

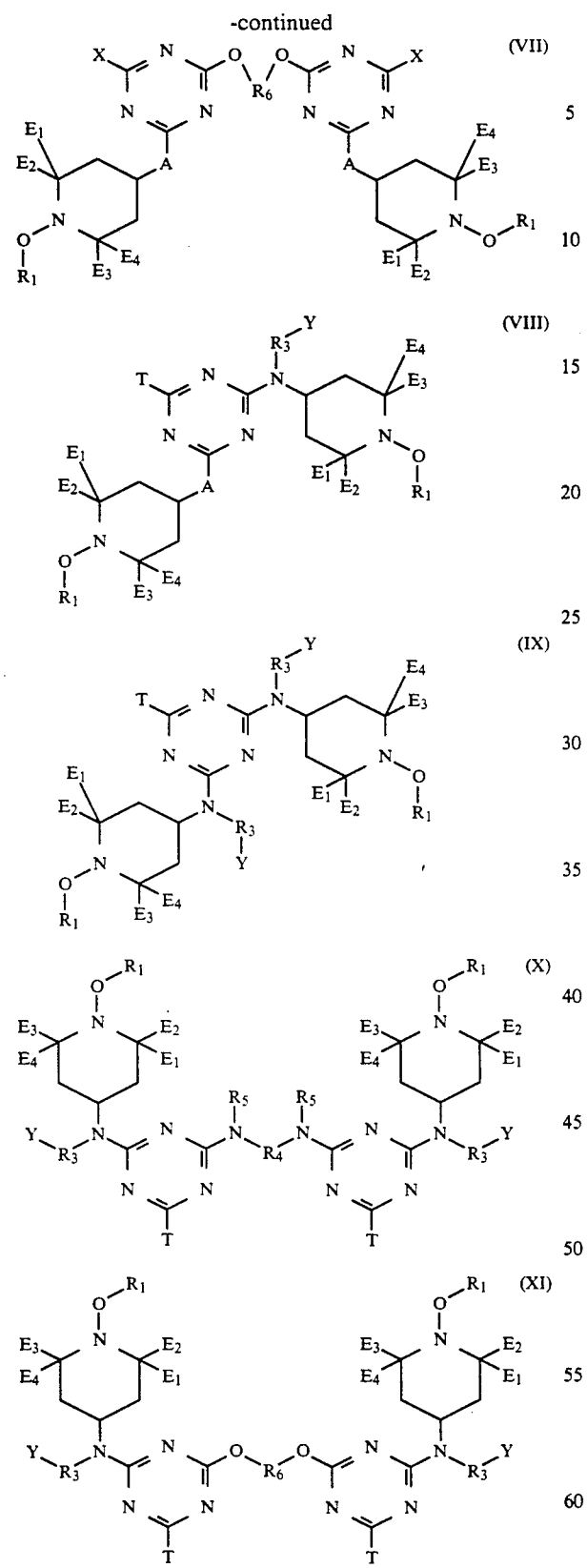

are pentamethylene, or $E_1$ and $E_2$; $E_3$ and $E_4$ each taken together are pentamethylene, $R_1$ is alkyl of 1 to 18 carbon atoms, cycloalkyl of 5 to 12 carbon atoms, a bicyclic or tricyclic hydrocarbon radical of 7 to 12 carbon atoms, phenylalkyl of 7 to 15 carbon atoms, aryl of 6 to 10 carbon atoms or said aryl substituted by one to three alkyl of 1 to 8 carbon atoms, $R_2$ is hydrogen or a linear or branched chain alkyl of 1 to 12 carbon atoms, $R_3$ is alkylene of 1 to 8 carbon atoms, or $R_3$ is —CO—, —CO—$R_4$—, —CONR$_2$—, or —CO—NR$_2$—$R_4$—, $R_4$ is alkylene of 1 to 8 carbon atoms, $R_5$ is hydrogen, a linear or branched chain alkyl of 1 to 12 carbon atoms, or

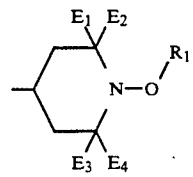

or when $R_4$ is ethylene, two $R_5$ methyl substituents can be linked by a direct bond so that the triazine bridging group —N($R_5$)—$R_4$—N($R_5$)— is a piperazin-1,4-diyl moiety, $R_6$ is alkylene of 2 to 8 carbon atoms or $R_6$ is

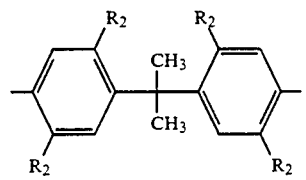

with the proviso that Y is not —OH when $R_6$ is the structure depicted above,

A is —O— or —NR$_7$— where $R_7$ is hydrogen, a straight or branched chain alkyl of 1 to 12 carbon atoms, or $R_7$ is

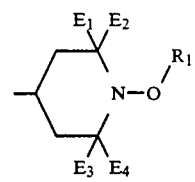

T is phenoxy, phenoxy substituted by one or two alkyl groups of 1 to 4 carbon atoms, alkoxy of 1 to 8 carbon atoms or —N($R_2$)$_2$ with the stipulation that $R_2$ is not hydrogen, or T is

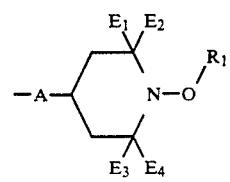

X is —NCO, —OH, —O—glycidyl, or —NHNH$_2$, and wherein
$E_1$, $E_2$, $E_3$ and $E_4$ are independently alkyl of 1 to 4 carbon atoms, or $E_1$ and $E_2$ are independently alkyl of 1 to 4 carbon atoms and $E_3$ and $E_4$ taken together Y is —OH, —NH$_2$, —NHR$_2$ where R$_2$ is not hydrogen; or Y is —NCO, —COOH, oxiranyl, —O—glycidyl, or —Si(OR$_2$)$_3$; or the combination R$_3$—Y— is —CH$_2$CH(OH)R$_2$ where R$_2$ is alkyl or said alkyl interrupted by one to four oxygen atoms, or R$_3$—Y— is —CH$_2$OR$_2$.

2. A composition according to claim 1 wherein the synthetic polymer of component (a) is an acid catalyzed or ambient temperature cured polymer selected from the group consisting of thermoset acrylic resins with melamine crosslinking agents, acrylic alkyd or polyester resins with isocyanate crosslinking agents or epoxy resins with carboxylic acid, anhydride or amine crosslinking agents.

3. A composition according to claim 2 wherein the compound of component (b) is bonded onto the polymer substrate of component (a) through a chemical bond derived from the chemical reaction of the functional group present in the compound of component (b) with an appropriately reaction functional group on the substrate polymer of component (a).

4. A composition according to claim 2 wherein the polymer of component (a) is a polyester polyurethane refinish enamel.

5. A composition according to claim 2 wherein the polymer of component (a) is a high solids thermoset acrylic enamel.

6. A composition according to claim 3 wherein the compound of component (b) is 2-[(2-hydroxyethyl)amino]-4,6-[N-(1-cyclohexyloxy-2,2,6,6-tetramethylpiperidin-4-yl)butylamino]-1,3,5-triazine.

7. A composition according to claim 3 wherein the compound of component (b) is 2[(2-hydroxyethyl)amino]-4,6-[N-(1-octyloxy-2,2,6,6-tetramethylpiperidin-4-yl)butylamino]-1,3,5-triazine.

8. A composition according to claim 3 wherein the compound of component (b) is N-{4,6-bis[(1-cyclohexyloxy-2,2,6,6-tetramethylpiperidin-4-yl)butylamino]-1,3,5-triazin-2-yl}-6-aminohexanoic acid.

9. A composition according to claim 3 wherein the compound of component (b) is N-{4,6-bis[(1-octyloxy-2,2,6,6-tetramethylpiperidin-4-yl)butylamino]-1,3,5-triazin-2-yl}-6-aminohexanoic acid.

10. A composition according to claim 3 wherein the compound of component (b) is 2-[bis(2-hydroxyethyl)amino]-4,6-bis[N-(1-cyclohexyloxy-2,2,6,6-tetramethylpiperidin-4-yl)butylamino]-1,3,5-triazine.

11. A composition according to claim 3 wherein the compound of component (b) is 2-[bis(2-hydroxyethyl)amino]-4,6-bis[N-(1-octyloxy-2,2,6,6-tetramethylpiperidin-4-yl)butylamino]-1,3,5-triazine.

* * * * *